United States Patent [19]

Liff

[11] Patent Number: 4,534,961
[45] Date of Patent: Aug. 13, 1985

[54] WAX BASE MAKEUP COMPOSITION

[76] Inventor: Lawrence J. Liff, 6502 N. Central #A-101, Phoenix, Ariz. 85012

[21] Appl. No.: 312,934

[22] Filed: Oct. 19, 1981

Related U.S. Application Data

[63] Continuation of Ser. No. 909,575, May 25, 1978, abandoned.

[51] Int. Cl.³ .................... A61K 7/021; A61K 7/025; A61K 7/031
[52] U.S. Cl. ....................... 424/63; 424/64; 514/772
[58] Field of Search ............................ 424/63

[56] References Cited

U.S. PATENT DOCUMENTS

| | | | |
|---|---|---|---|
| 2,936,245 | 5/1960 | Osipow et al. | 424/362 X |
| 3,162,575 | 12/1964 | Lang | 424/DIG. 5 |
| 3,444,291 | 5/1969 | Bivans | 424/358 X |
| 3,873,687 | 3/1975 | Demko | 424/63 X |
| 4,061,780 | 12/1977 | Yoshida et al. | 424/358 |

FOREIGN PATENT DOCUMENTS 1128312  9/1968  United Kingdom ................. 424/63

OTHER PUBLICATIONS

Merck Index, 10/1968, p. 1130.
Colour Index, 3/1958, vol. 3, p. 3635.
Poucher Perfumes, Cosmetics & Soaps, 1929, vol. II, p. 422.
Federal Regulations, Title 21, Chapter 1, pp. 173 to 175, 195, 196, 210 and 211.

*Primary Examiner*—Dale R. Ore
*Attorney, Agent, or Firm*—Woodling, Krost, Rust & Hochberg

[57] ABSTRACT

A wax base makeup composition primarily for use by children in creating various disguises. The composition consists essentially of from 85 to 92% of amber microcrystalline wax intimately admixed with 8 to 15% petrolatum. Artificial coloring materials are added and a copper activated zinc sulfide pigment may be added.

7 Claims, No Drawings

WAX BASE MAKEUP COMPOSITION

This is a continuation of application Ser. No. 909,575 filed May 25, 1978, now abandoned.

The present application discloses a unique combination of ingredients which when combined comprise a solid base formulation for use in multiple makeup functions. These are primarily used by children in creating scars and otherwise making up or changing parts of their faces to create various disguises. The essential formulation for the solid base makeup is quite critical in its specific materials and is also critical from the standpoint of the amounts of the materials that are utilized.

The basic formulation is capable of being modified within limits by the addition of materials that are disclosed herein to perform the function of providing the multiple makeup uses.

One of the makeup formulations which is disclosed herein has been developed with substantial experimentation so as to provide a safe toy for use by children in creating scars and building up parts of the face to make a disguise.

A variation of the basic formulation provides another disguise variation that can be used as a safe toy by children in creating a "lost tooth effect" in arriving at a disguise.

A still further variation of the basic solid base formulation provides the incorporation of a pigment type ingredient that can be used to disguise the face but which material permits the disguise to glow in the dark after having been exposed to a bright light.

In accordance with the teachings of the present invention the basic solid base formulation for multiple makeup uses comprises in combination a mixture of from 85 to 92% of amber, microcrystalline wax intimately admixed with on the order of 8-15% of white petrolatum.

The wax referred to and used in this invention is a plastic wax which is petroleum derived and refined to a ductile, flexible condition. This wax is less crystalline than normal paraffin waxes due to its lower concentration of n-paraffinic hydrocarbons and higher concentration of branched and napthenic hydrocarbons. The wax used in this invention contains about 20–40% n-paraffinic hydrocarbons. The following are some typical properties of the wax used herein.

| | |
|---|---|
| Melting Point | 175° F. |
| Congealing Point | 164° F. |
| Density at 75° F. | 0.9254 g/cc |
| Density at 210° F. | 0.7668 g/cc. |
| Viscosity at 210° F. (ASTM D-88) | 85 SUS |
| Penetration at 77° F. (ASTM D-1321) | 29 |
| Flash Point | 560° F. |

Typical physical characteristics of the petrolatum used in this invention are: Melting point 127°–137° F.; ASTM Consistency 180/210; Saybolt Viscosity at 210° F. 60/80; and ASTM Color ½.

Starting with this basic wax base formulation as just above recited, a material for use by children or others in creating a disguise such as a scar or building up other parts of the face for various disguise makeups can be formulated by making a 100 lb. batch of the composition as indicated in Table I.

TABLE I

| CHEMICAL ANALYSIS | PER 100 lb. BATCH |
|---|---|
| 85% Microcrystalline Wax | 85 lbs. |
| 15% Petrolatum USP, White | 15 lbs. |

Colorants may be added to this formulation to create a desired effect. In order to accomplish this, various artificial colorants are added to each 100 pound batch of the formulation. The amounts, color blends, and intensities of these added dyes are determined by the intended end use for that 100 pound batch of makeup composition. The color standards for these dye materials are set by the World Health Organization. These colors are listed in the Code of Federal Regulations, Title 21, Parts 1–9. The amount of colorant used is on the order of 0.1% (0.001) of the total batch weight.

The method of incorporating the materials together which are enumerated in Table I is set forth hereinbelow.

METHOD STEPS FOR MIXING 100 LB. BATCH OF INGREDIENTS OF TABLE I

1. Clean, disinfect, and rinse all mixing equipment.
2. Turn heat control in mixing container to 250° F.
3. Add 15 lbs. petrolatum to container.
4. Add 85 lbs. microcrystalline wax.
5. Allow mixture to melt completely for about 45 minutes.
6. Add dye materials and stir in thoroughly and allow to cool down to a constant temperature of 180° F.

In order to utilize the composition of Table I made by the method indicated immediately above, one takes a small lump of the material and kneads into one's hand to soften it substantially and then it is applied to the part of the face or body that one desires to build up or work into the disguise. The material is worked into the desired shape and the edges are blended to that portion of the body to which the material is applied. The particular material can be used to simulate cuts, wounds, burns, gashes, abrasions, bullet holes and any number of other deformities such as removing the end of a finger. The material is self-adhering when utilized in the composition and proportions indicated in Table I. The chemical composition and degree of softness allows it to hold onto the skin without any other adhesive for substantial periods of time. The material can also be used as an adhesive for example by placing a dab of the material on the back of one's fingernail one can attach artificial fingernails to one's real nails. As another example one can apply a small ball of the material to one's nose thereby forming a wart and similar uses too numerous to mention can be used with the material.

Another variation of the use of the basic solid base formulation is illustrated in Table II hereinbelow.

TABLE II

| CHEMICAL ANALYSIS | PER 100 lb. BATCH | |
|---|---|---|
| 92% Microcrystalline Wax | 92 lbs. | |
| 8% Petrolatum USP, White | 8 lbs. | |
| Artificial Coloring | 15 oz. | Black lake |

METHOD STEPS FOR MIXING 100 LB. BATCH OF INGREDIENTS OF TABLE II

1. Clean, disinfect, and rinse all mixing equipment.
2. Turn heat control in mixing container to 250° F.
3. Add 8 lbs. petrolatum to container.

4. Add 92 lbs. microcrystalline wax.

5. Allow mixture to melt completely for about 45 minutes.

6. Turn thermostat to 180° F. for consistent mix.

7. 25 lbs. of the 100 lb. batch of 180° F. material is poured into a stainless steel bucket from the mixing container. The material is then emptied into a filling hopper of a filling apparatus. Turn on the filling hopper agitator of the filling apparatus. Now, add 3.75 oz. of artificial coloring (Black Lake). This process is repeated four (4) times for every 100 lb. batch. The agitator, used to keep the coloring in suspension, should cause a shallow whirlpool at the center, to be of any use. It is necessary that the agitator be kept running constantly during the filling operation, or whenever there is material in the filling hopper. Coloring can be added only after the agitator is on.

This particular composition, for the sake of example, has a makeup use for children whereby the children can create a lost tooth effect in making a disguise.

To utilize the material identified in Table II the child rolls a small piece of the material into a ball about the size of a small pea after which the child dries off a tooth and applies the material to the middle of the tooth. The material is then spread around and about the entire tooth thereby giving the appearance that the tooth has been removed.

The method of making the formulation covered in Table II is quite critical in at least two areas. It is extremely important to get the composition to a temperature of at least 180° F. before the material is added to the filling hopper of the filling apparatus. It is also essential that the hopper agitator of the filling apparatus be completely agitated otherwise the coloring material will fall out of the basic formulation and when the containers which are to carry the product to the ultimate consumers are filled there will be no colorant in the basic formulation.

A still further formulation can be utilized by starting with the basic solid base formulation and this is illustrated in Table III which appears hereinbelow.

TABLE III

| CHEMICAL ANALYSIS | PER 100 lb. BATCH |
| --- | --- |
| 92% Microcrystalline Wax | 92 lbs. |
| 8% Petrolatum USP, White | 8 lbs. |
| Artificial Coloring | .0012 oz. |

Approximately 5 lbs. of zinc sulfide (copper activated) is added to the 100 lb. (approx.) batch immediately above in the manner indicated hereinafter. The copper activated zinc sulfide is a phosphorescent pigment which has a daylight color of green-yellow and has an afterglow of about 20 hours. The material used in this invention has a boiling point of 3850° F. at 150 atmospheres; a solubility in water at 64.4° F. of $2.8 \times 10^{-4}\%$ and a specific gravity of 4.087.

The method steps that are necessary to formulate the composition of Table III into a usable commercial product are given hereinbelow.

METHOD STEPS FOR MIXING 100 LB. BATCH OF INGREDIENTS OF TABLE III

1. Clean, disinfect and rinse all mixing equipment.
2. Turn heat control in mixing container to 250° F.
3. Add 8 lbs. petrolatum to container.
4. Add 92 lbs. microcrystalline wax.

5. Allow mixture to melt completely for about 45 minutes.

6. Add artificial coloring, stir in thoroughly and allow to cool down to a constant temperature of 180° F.

7. Turn thermostat to 180° F. for consistent mix.

8. 25 lbs. of the 100 lb. batch of 180° F. material is poured into a stainless steel bucket from the mixing container. The material is then emptied into a filling hopper of a filling apparatus. Turn on the filling hopper agitator of the filling apparatus. Now, add 1.25 lbs. of zinc sulfide pigment. This process is repeated four (4) times for every 100 lb. batch. The agitator, used to keep the zinc sulfide pigment in suspension, should cause a shallow whirlpool at the center, to be of any use. It is necessary that the agitator be kept running constantly during the filling operation, or whenever there is material in the filling hopper. Zinc sulfide pigment can be added only after the agitator is on.

This particular formulation is capable of essentially the same uses enumerated in the composition of Table I; however, the zinc sulfide pigment which is added to the formulation permits the composition to glow in the dark after having been exposed to a bright light. This material with the precise ingredients which have been set forth hereinabove is a completely safe toy for the use of children in creating scars and other makeup uses. The material can additionally be used for the purpose of making other parts of the body glow such as the teeth and it can also be adhered to toys, posters and other items for a glow in the dark effect.

As in the formulation disclosed in Table II hereinabove, it is necessary that the composition be heated to a temperature of at least 180° F. as recited in step 7 of the method because it must reach at least this temperature or it will not adequately flow. It is also extremely critical that the hopper agitator on the filling apparatus be constantly agitated when the material at 180° F. is added thereto because if this is not done the zinc sulfide pigment will fall out of the basic composition and when the composition is added to the individual containers which are to transport the product to its ultimate consumers there will not be any zinc sulfide pigment present and the product will not glow in the dark as represented.

It will therefore be seen that a solid base formulation has been disclosed which can be utilized in various makeup uses which solid base formulation comprises from 85 to 92% of amber, microcrystalline wax intimately admixed with on the order of 8 to 15% petrolatum. When the various additional materials are added to this basic formulation as indicated in Tables I, II and III hereinabove various end products susceptible of various makeup uses is provided all of which can be utilized in the manner indicated.

These basic makeup formulations enumerated in Tables I, II and III are quite novel in that they are quite safe for use by children when applied to various exterior portions of the body yet are not harmful if accidentally ingested. Additionally the formulations set forth hereinabove are relatively inexpensive to produce and therefore are relatively inexpensive to the ultimate consumer thereby providing a large mass use of the product with resultant benefit to the public.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A solid base formulation for multiple makeup uses including in combination a mixture consisting of on the order of 85 to 92% of amber, microcrystalline wax intimately admixed with on the order of 8 to 15% of petrolatum, said petrolatum having a melting point of 127°–137° F.

2. A solid base formulation as claimed in claim 1 wherein an artificial coloring material is added to the mixture in an amount in the range of from 0.001 oz. to 15 oz. for each 100 pounds of said solid base formulation.

3. A solid base formulation as claimed in claim 2 wherein said zinc sulfide is copper activated.

4. A solid base formulation as claimed in claim 2 wherein copper activated zinc sulfide is added.

5. The method of making a 100 pound batch of a solid base makeup formulation consisting of the steps of adding 8 to 15 pounds of white petrolatum to a container which is heated to about 250° F., said petrolatum having a melting point of 127°–137° F.;

adding 85 to 92 pounds of amber, microcrystalline wax to the white petrolatum;

allowing the mixture of the two materials to melt together for about 45 minutes at 250° F.;

adding an artificial coloring material to the mixture with constant stirring;

and cooling the mixture down to a consistent temperature of 180° F. with constant stirring.

6. The method as claimed in claim 5 wherein about 25% of said mixture cooled to 180° F. is added to the hopper of a container filling apparatus and 1.25 pounds of copper activated zinc sulfide is added with constant agitation of said mixture, said agitation is continued until the hopper is emptied.

7. The method as claimed in claim 5 wherein about 25% of said mixture cooled to 180° F. is added to the hopper of a container filling apparatus and 3.75 oz. of an artificial colorant is added with constant agitation of said mixture, said agitation is continued until the hopper is emptied.

* * * * *